United States Patent
Stürmer

(10) Patent No.: US 6,551,806 B1
(45) Date of Patent: Apr. 22, 2003

(54) PREPARING ENZYME-CONTAINING POLYMERS BY REACTING AN ENZYME IN ORGANIC SOLUTION WITH CROSSLINKING COMPOUNDS

(75) Inventor: Rainer Stürmer, Rödersheim-Gronau (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/720,914

(22) PCT Filed: Jul. 2, 1999

(86) PCT No.: PCT/EP99/04590

§ 371 (c)(1),
(2), (4) Date: Jan. 2, 2001

(87) PCT Pub. No.: WO00/05354

PCT Pub. Date: Feb. 3, 2000

(30) Foreign Application Priority Data

Jul. 21, 1998 (DE) .......................................... 198 32 547

(51) Int. Cl.$^7$ ............................. C12P 7/62; C12P 1/00; C12P 41/00; C12N 11/08; C12N 11/04
(52) U.S. Cl. ...................... 435/135; 435/41; 435/134; 435/155; 435/177; 435/180; 435/182; 435/280
(58) Field of Search ................................. 435/134, 135, 435/177, 180, 182, 280, 41, 155

(56) References Cited

U.S. PATENT DOCUMENTS

| | | | |
|---|---|---|---|
| 3,672,955 A | 6/1972 | Stanley | 195/68 |
| 4,342,834 A | 8/1982 | Wood et al. | 435/182 |
| 4,634,671 A | 1/1987 | Sakata et al. | 435/188 |
| 5,482,996 A | 1/1996 | Russell et al. | 525/54 |
| 5,756,321 A | 5/1998 | Schudok et al. | 435/123 |

FOREIGN PATENT DOCUMENTS

DE 195 05 672 8/1996

OTHER PUBLICATIONS

LeJeune et al. "Dramatically Stabilized Phophotriesterase–Polymers for Nerve Agent Degradation" Biotechnology and Bioengineering vol. 54 No. 2, (1997) pp. 105–114.

Dias et al. "Production of Ethyl Butyrate by *Candida rugosa* Lipase Immobilized in Polyurethane" Biocatalysis vol. 5 pp. 21–34.

Koshiro et al. "Stereoselective esterification of dl–menthol by polyurethane–entrapped lipase in organic solvent" Journal of Biotechnology vol. 2, (1985) pp. 47–57.

*Primary Examiner*—David M. Naff
(74) *Attorney, Agent, or Firm*—Keil & Weinkauf

(57) ABSTRACT

Enzyme-containing polymers are prepared by an anhydrous process of direct reaction of an enzyme in organic solution with crosslinking organic compounds having terminal reactive groups. In a first step, the enzyme is reacted in an organic solvent with a bifunctional monomer such as p-phenylene diisocyanate, 4-methyl-m-phenylene diisocyanate or 4,4'-methylenebisphenyl diisocyanate, and in a second step a bifunctional amine such as N-phenylethylenediamine, 1,6-diaminohexane, N,N'-diethyl-ethylenediamine or 1,4-diaminobutane is added. The enzyme-containing polymers are used as catalysts in chemical reactions such as acylation or enantioselective acylation of alcohols.

14 Claims, No Drawings

PREPARING ENZYME-CONTAINING POLYMERS BY REACTING AN ENZYME IN ORGANIC SOLUTION WITH CROSSLINKING COMPOUNDS

BACKGROUND OF THE INVENTION

1. Field of the Invention

The present invention relates to novel enzyme-containing polymers comprising at least one of the following structural elements:

Structural Element 1

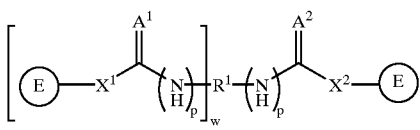

Structural Element 2

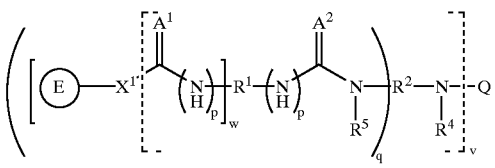

where the abbreviations and symbols have the following meanings:

E enzyme $X^1$, $X^2$ independently of one another oxygen, sulfur or NH from a functional group of the enzyme Q hydrogen or the group:

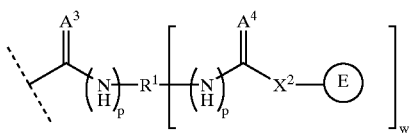

$A^1$, $A^2$, $A^3$, $A^4$ independently of one another oxygen or sulfur p 0 or 1, with the proviso that $A^1$, $A^2$, $A^3$, $A^4$ are oxygen when p is 0 w 1–4 q 1–4 v 1–100

$R^1$ an alkane, alkene, cycloalkane, cycloalkene, arene, arylalkane, diaryl ether, diaryl thioether or diarylamine group which is bonded 2 to 5 times, it being possible for the aromatic or nonaromatic cyclic groups in turn to be substituted by one to four $C_1$–$C_4$-alkyl, $C_1$–$C_4$-haloalkyl and/or halogen radicals, $R^2$ an alkane, alkene, cycloalkane, cycloalkene, arene, arylalkane, dialkyl ether, dialkyl thioether, diaryl ether, diaryl thioether, diarylamine or piperazinedialkanediyl group which is bonded 2 to 5 times, it being possible for the aromatic or nonaromatic cyclic groups in turn to be substituted by one to four $C_1$–$C_4$-alkyl, $C_1$–$C_4$-haloalkyl and/or halogen radicals, $R^4$ und $R^5$ independently of one another hydrogen, a $C_1$–$C_4$-alkyl, aryl or alkylaryl group.

The present invention also relates to the preparation and use of the enzyme-containing polymers.

The enzyme-containing polymers are employed as enzyme catalysts in chemical reactions. Compared with the free enzymes, the immobilized enzymes are distinguished by an increased stability and useful life when reactions are carried out continuously and batchwise, and by easy recovery of the catalytically active species in the case of batchwise reactions.

2. Description of the Related Art

It is known to incorporate enzymes into polymers by covalent bonding with retention of the activity. It is further known to use polyurethanes, polyureas and polyamides as polymeric carrier material. U.S. Pat. No. 5,482,996 describes protein-containing polyurethanes, polyureas, polyamides and polyesters. In this case, the proteins are transferred from the aqueous solvent system into the organic solvent system, with retention of the activity, by attaching an amphiphilic spacer (polyalkylene oxide) which has the terminal functional group suitable for the type of polymerization. The monomers are then reacted with the functional group of the spacer. This method makes only low coverage possible and is moreover very elaborate and costly because there is no direct incorporation of the enzymes into the polymer, but the attachment of the amphiphilic spacer unit comprises a preceding additional step.

U.S. Pat. No. 3,672,955 discloses the preparation of enzymes immobilized in polyurethane, where there is initial preparation of amphiphilic isocyanate prepolymers bridged with polyether and polyesterpolyol units, and these are emulsified and reacted in a water-immiscible solvent with the aqueous enzyme solution. The contact with water converts the isocyanates which have not reacted with the functional groups of the enzymes into unstable carbamic acid groups which then decompose into the corresponding amines with elimination of $CO_2$. The resulting amino groups react with isocyanate groups which are still present, to give crosslinking, and the $CO_2$ produced leads to foaming of the polymer mass. U.S. Pat. No. 4,342,834 follows the analogous prepolymer strategy of transferring the polymerization into aqueous systems, the difference from U.S. Pat. No. 3,672,955 being that the reaction is completely carried out in aqueous solution.

The use of the amphiphilic prepolymers Hypol® which is analogously bridged with polyalkylene oxide units (produced by reacting a polyether- or polyesterpolyol with polyisocyanates in the presence of linking reagents) and PU-3® (prepolymer saturated with two terminal TDI units and containing polyethylene oxide and polypropylene oxide units as spacer) for immobilizing a number of enzymes from aqueous solution has been described in scientific articles.

It was possible to use these amphiphilic prepolymers to immobilize phosphotriesterases from aqueous solution for breaking down neurotoxins (K. E. Lejeune et al., Biotechnology and Bioengineering 1997, 54, 105–114). Lipases immobilized from aqueous solution with prepolymers have been used for the acylation (S. F. Dias et al., Biocatalysis 1991, 5, 21–34.) and for the enantioselective acylation (S. Koshiro et al., Journal of Biotechnology 1985, 2, 47–57) of alcohols in organic solution.

In all these processes, the polymerization (immobilization of the enzyme) is carried out in the presence of water with prepolymers. This has several disadvantages:

The amphiphilic prepolymers must be prepared separately.

Only short useful lives are achieved with prior art enzyme-containing polymers.

Only low loading densities with active enzyme species are achieved. The typical loading of a polymer with enzyme in the abovementioned studies is a maximum of 1% of the total mass. Low space-time yields (STY) result from this.

SUMMARY OF THE INVENTION

It is an object of the present invention to remedy the deficiencies described and to provide novel enzyme-containing polymers which have been prepared by a simplified process and have optimized properties, such as longer useful life and higher loading density with catalytically active enzyme species.

We have found that these objects are achieved by the enzyme-containing polymers according to the invention described at the outset.

The structural elements are produced by reacting the functional groups (amino, hydroxyl, mercapto) located on the enzyme surface with monomers having at least bifunctionally reactive groups, and subsequently adding at least bifunctional amines.

DETAILED DESCRIPTION OF THE INVENTION

The enzymes are to be regarded as at least monofunctional, usually polyfunctional, amines, alcohols and/or thiols. They can be obtained, for example, from organisms such as fungi, bacteria (Gram+ or Gram−), yeasts or mammals, and have an enzymatic activity in organic solvents.

Examples which may be mentioned are hydrolases such as esterases, lipases, amidases, proteases and haloperoxidases, aminotransferases, aspartate aminotransferases, pyruvate decarboxylases, lyases/laccases, benzene dioxygenase, aspartases, dehydrogenases, fumarases, dehalogenases, amino-acid dehydrogenases, oxygenases, aminopeptidases, aminoamidases, alkylaminopeptidases and racemases.

Preference is given to lipases from *Aspergillus niger, Aspergillus oryzae, Candida antarctica, Candida cylindracea, Candida lipolytica, Candida utilis, Candida rugosa, Mucor javanicum, Mucor miehei, Rhizomucor miehei, Rhizopus arrhizus, Rhizopus delemar, Rhizopus niveus, Penicillium acylase, Penicillium roqueforti, Thermus aquaticus, Thermus flavus, Thermus thermophilus, Chromobacterium viscosum, Pseudomonas putida, Pseudomonas fluorescens, Pseudomonas cepacia,* and pig pancreatic lipase (PPL) and wheat germ lipase, esterases from *Bacillus subtilis, Bacillus stearothermophilus, Bacillus thermoglucosidasius, Candida lipolytica, Mucor miehei,* equine liver, porcine liver, *Saccharomyces cerevisiae, Thermoanaerobium brockii, Elektrophorus electricus,* proteases such as subtilisin, thermolysin, subtilisin Carlsberg, nagarse or from *Bacillus subtilis, Tritirachium alba, Aspergillus oryzae,* Aspergillus sp., benzene dioxygenase from Pseudomonads, Alcaligenes sp., Micrococcus sp., *Pseudomonas oleovorans,* dehalogenases from *Pseudomonas putida,* oxygenases from *Pseudomonas oleovorans, Corynebacterium equi, Nocardia carallina,* Mycobacter, Xanthobacter, aminoamidases and alkylaminopeptidases from Mycobacterium, dehydrogenases from *Pseudomonas putida* and nitrilases and nitrile hydratases from *Aspergillus niger* JCM 1925, Fusarium sp. MY-2, *Rhodococcus rhodocrus* J 1, K22, PA 34 and NCIB 11216, *Pseudomonas chlororaphis* B 23, Corynebacterium sp. N-774.

The lipase from *Burkholderia plantarii* is particularly preferred. Structural element 1 describes the simplest case in which two enzymes are linked by an at least bifunctional monomer unit. X ($X^1$ or $X^2$) represents the reacted functional group (hydroxyl, mercapto or amino group) on the enzyme surface. X can be according to the invention oxygen, sulfur or NH.

The case where p=1 corresponds to linkage of the enzyme to an at least bifunctional and at most pentafunctional (w a maximum of 4) isocyanate (A=oxygen) ($A^1, A^2, A^3$ or $A^4$), isothiocyanate (A=sulfur) or mixed isocyanate/isothiocyanate (A=oxygen or sulfur) via a urethane (X=oxygen, A=oxygen), thiocarbamic acid O-ester (thiourethane; X=oxygen, A=sulfur), urea (X=NH, A=oxygen), thiourea (X=NH, A=sulfur), thiocarbamic acid S-ester (X=sulfur, A=oxygen) or dithiocarbamic acid diester (X=sulfur, A=sulfur) group.

The case where p=0 corresponds to linkage of the enzyme to an at least bifunctional and at most pentafunctional (w a maximum of 4) active ester via an ester (X=oxygen), amide (X=NH) or thiolcarboxylic ester (X=sulfur) group.

$R^1$ represents an alkane, alkene, cycloalkane, cycloalkene, arene, arylalkane, diaryl ether, diaryl thioether or diarylamine group which carries the functional groups and is bonded 2 to 5 times, it being possible for the aromatic or nonaromatic cyclic groups in turn to be substituted by one to four $C_1$–$C_4$-alkyl, such as methyl, ethyl, propyl, isopropyl, n-butyl, isobutyl or t-butyl, and/or $C_1$–$C_4$-haloalkyl, such as trichloromethyl, trifluoromethyl or trifluoroethyl, and/or halogen radicals, such as Cl, Br, I or F. Preferred $R^1$ radicals are the basic organic moieties underlying the corresponding polyisocyanate or isothiocyanate monomers known from polyurethane chemistry. The following specific structures may be listed as particularly preferred, the linkage points being indicated by a dash:

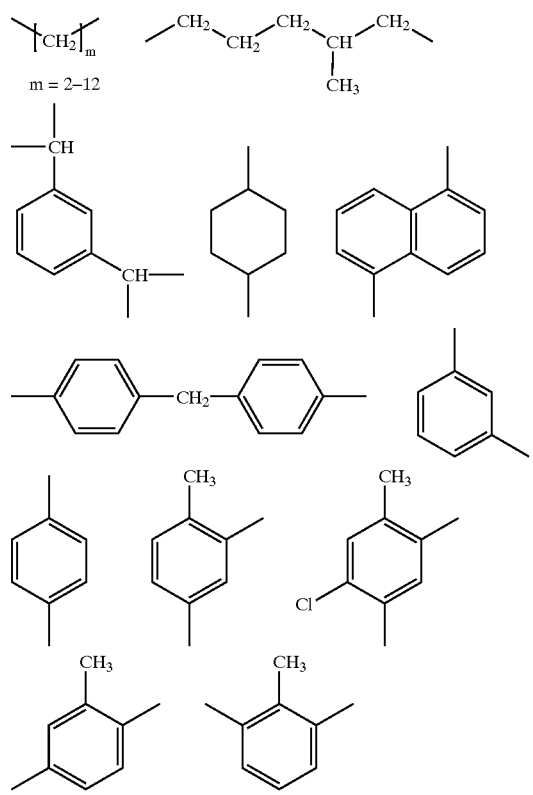

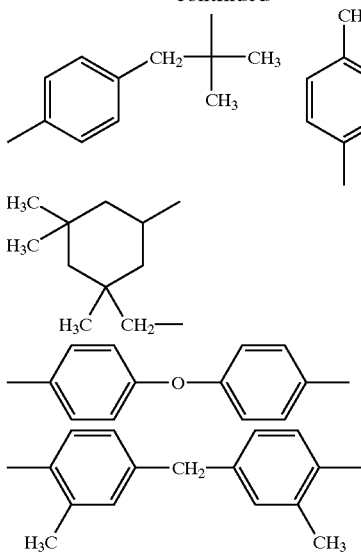

The enzymes, symbolized by the letter E in a circle, may be various enzyme molecules or different binding sites on the same enzyme molecule. In the particular case where w>1, that is to say branched polyfunctional monomers are used, the enzyme symbols may also represent various adjacent binding sites on the same enzyme molecule.

Structural element 2 takes account of the additional incorporation of the at least bifunctional amines. The linkage of the at least bifunctional monomers to the enzyme is analogous to Structural element 1 and has been described there. In the simplest case (v=0), a bifunctional amine (q=1) links two at least bifunctional monomers, which are bonded terminally by the appropriate functional group to the enzyme, via a urea ($A^1$=oxygen, p=1), thiourea (A=sulfur, p=1) or amide (A=oxygen, p=0) group. The unit [at least bifunctional monomer-at least bifunctional amine] may be repeated V times to form polyurea (A=oxygen, p=1), polythiourea (A=sulfur, p=1) or polyamide (A=oxygen, p=0) chains (w=1; q=1) or crosslinks (either w>1 or q>1 or w and q>1). The case Q=hydrogen covers the termination of a chain without linkage to another enzyme molecule.

$R^2$ is an alkane, alkene, cycloalkane, cycloalkene, arene, arylalkane, dialkyl ether, dialkyl thioether, diaryl ether, diaryl thioether, diarylamine or piperazinedialkanediyl group which carries the amino groups and is bonded 2 to 5 times, it being possible for the aromatic or nonaromatic cyclic groups in turn to be substituted by one to four $C_1$–$C_4$-alkyl, $C_1$–$C_4$-haloalkyl and/or halogen radicals, e.g. as mentioned above for $R^1$.

Preferred radicals are the basic organic moieties underlying the corresponding polyamine monomers known from polyurethane and polyamide chemistry. The following specific structures may be listed as particularly preferred:

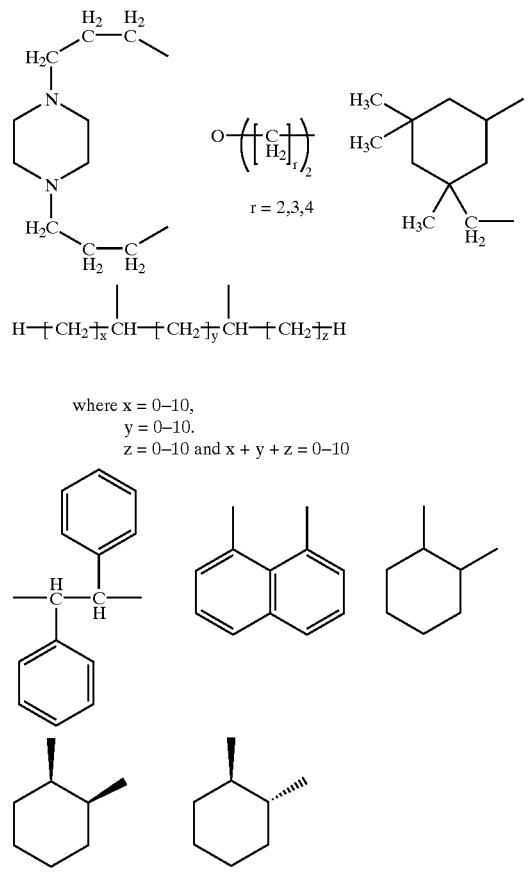

Depending on the incorporation of primary or secondary at least bifunctional amines, $R^4$ and $R^5$ are, independently of one another, hydrogen or a $C_1$–$C_4$-alkyl radical such as methyl, ethyl, propyl, isopropyl, n-butyl, isobutyl, t-butyl or an aryl or alkylaryl radical, such as phenyl or $C_1$–$C_4$-substituted phenyl such as tolyl.

It is also necessary to take into account with Structural element 2 that the enzymes, symbolized by the letter E in a circle, may be various enzyme molecules or different binding sites on the same enzyme molecule.

The contents of the enzyme by weight in the polymeric carrier are preferably between 0.01% by weight and 50% by weight, particularly preferably between 1% by weight and 10% by weight, based on the total mass. As shown in Example 3, the enzyme activity and the useful life decrease if the loading is less (0.5%) than 1%. By contrast, greater loading (5%) than 1% does not result in a decrease in the enzyme activity and the useful life. The greater loading allows a higher space-time yield (STY) to be achieved in the enzyme-catalyzed reactions described hereinafter.

It has additionally been found that the enzyme-containing polymers according to the invention are particularly advantageously obtained in a simplified, anhydrous process by direct reaction of the enzyme in organic solution with crosslinking organic compounds with terminal reactive functional groups. This entails reacting the enzyme in an organic solvent in the first step with the at least bifunctional monomer of the formula I $$R^1(X)_s(Y)_t \qquad \text{I}$$

where
- $R^1$ is an alkane, alkene, cycloalkane, cycloalkene, arene, arylalkane, diaryl ether, diaryl thioether or diarylamine group which is bonded 2 to 5 times, it being possible for the aromatic or nonaromatic cyclic groups in turn to be substituted by one to four $C_1$–$C_4$-alkyl, $C_1$–$C_4$-haloalkyl or halogen radicals, and
- X is the isocyanate (—NCO) functional group and
- Y is the isothiocyanate (—NCS) functional group with $s \geq 0$ and $t \geq 0$ and $5 \geq s+t \geq 2$ or
- X=Y is the —$COR^3$ functional group with $5 \geq s+t \geq 2$,
  in which $R^3$ is a leaving group which can be displaced by the amino, hydroxyl or mercapto functionality of the enzyme, and adding in a 2nd step an at least bifunctional amine or a mixture of at least bifunctional amines.

Organic solvents mean according to the invention aprotic solvents such as aliphatic, aromatic, optionally halogenated hydrocarbons, and ethers. Preferred organic solvents are those which are inert toward the at least bifunctional monomers, dissolve the at least bifunctional monomers, and do not denature the enzyme. Particularly preferred organic solvents are toluene, benzene, chloroform, methylene chloride, hexane, heptane, diethyl ether and methyl t-butyl ether (MTBE), dioxane, THF and halogenated aromatic compounds such as chlorobenzene.

The enzymes are suspended in an organic solvent and, in a first step, reacted with an at least bifunctional monomer. The monomer has as functional groups at least two and not more than five, particularly preferably two or three, isocyanate and/or isothiocyanate, or at least 2 and a maximum of five, particularly preferably two or three, active ester groups of the formula —$COR^3$ in which $R^3$ is a leaving group which can be displaced by the amino, hydroxyl or mercapto functionality of the enzyme. Examples which may be mentioned of active ester groups and thus of acyl donors are carbonyl chlorides, carboxylic anhydrides, carboxylic esters such as N-hydroxysuccinimide esters of carboxylic acids, phenol esters and halophenol esters such as pentafluorophenol esters and trichlorophenol esters. Accordingly, examples which may be mentioned of the leaving group $R^3$ are halides such as $Cl^-$, $Br^-$, $I^-$, carboxylates such as acetates and propionates or alcoholates such as N-succinimidoxide, phenolates, halophenolates such as pentafluorophenolate, trichlorophenolates or 1-benzotriazoloxides. The functional groups on the enzyme surface (amino, hydroxyl and/or mercapto groups) react with the terminal isocyanate and/or isothiocyanate functionalities of the monomers to form urethane, thiocarbamic acid O-ester(thiourethane), urea, thiourea, thiocarbamic acid S-ester and/or dithiocarbamic acid diester linkages. In analogy to this on use of the polyfunctional active ester monomers there is formation with the functional groups on the enzyme surface (amino, hydroxyl and/or mercapto groups) of amide (Jerry March, Advanced Organic Chemistry, 1992, 4th edition, John Wiley & Sons, New York, pp. 417–425), ester (Jerry March, Advanced Organic Chemistry, 1992, 4th edition, John Wiley & Sons, New York, pp. 392–398) and/or thiolcarboxylic ester linkages (Houben-Weyl, Volume IX, 4th edition, pp.753–756). These linkage types may occur in any combination depending on the presence and number of the respective functional groups on the enzyme surface and the monomer used.

The diisocyanate, polyisocyanate, diisothiocyanate, polyisothiocyanate, mixed polyisocyanates/isothiocyanate or bi- to pentafunctional active ester monomers used are alkane, alkene, alkyne, cycloalkane, cycloalkene, arene, alkylarene, arylalkane, diaryl ether, diaryl thioether or diarylamine compounds, it being possible for the aromatic or nonaromatic cyclic groups in these compounds in turn to be substituted by one to four $C_1$–$C_4$-alkyl, $C_1$–$C_4$-haloalkyl and/or halogen radicals. Preferred radicals are the diisocyanates, polyisocyanates, diisothiocyanates, polyisothiocyanates and mixed polyisocyanates/polyisothiocyanates or polyfunctional carboxylic acid or carboxylic ester derivatives which are known from polyurethane chemistry and have the basic moieties analogous to the polyisocyanates described, and have the active ester groups described above as functional groups in place of the isocyanate or isothiocyanate groups. Particularly preferred monomers are 1,4-diisocyanatobutane,
1,6-diisocyanatohexane,
1,8-diisocyanatooctane,
1,12-diisocyanatododecane,
1,5-diisocyanato-2-methylpentane,
1,3-bis-isocyanatomethylbenzene,
trans-1,4-diisocyanatocyclohexane,
1,5-diisocyanatonaphthalene,
4,4'-methylenediphenyl diisocyanate,
1-(p-isocyanatophenyl)-2-isocyanato-2-methylpropane,
tolylene 2,4-diisocyanate (4-methyl-m-phenylene diisocyanate),
tolylene 2,5-diisocyanate,
tolylene 2,6-diisocyanate,
1,3-diisocyanatobenzene,
1,4-diisocyanatobenzene (p-phenylene diisocyanate),
4,4'-oxydiphenyl diisocyanate,
3,3'-bistolyl-4,4'-diisocyanate,
3,3'-dimethyl-4,4'-diisocyanatodiphenylmethane,
2,4-diisocyanato-5-chlorotoluene,
isophorone diisocyanate and the analogous polyisothiocyanates or analogous mixed polyisothiocyanates/isocyanates.

In the case where it is advantageous to obtain the enzyme-containing polymer as foam (e.g. to increase the internal surface area) it is possible simultaneously with the addition of the monomer to add physical blowing agents such as hydrocarbons, in particular methane, ethane, ethylene, propane, propylene, pentane, cyclopentane, cyclohexane, or halogenated hydrocarbons, in particular trichlorofluoromethane, chloromethane, dichlorodifluoromethane, dichlorofluoromethane, chlorodifluoromethane, chloroethane, dichlorotetrafluoroethane, octafluorocyclobutane, hexafluoropropane, 1,1-difluoro-2,2-dichloroethane, 1,2-difluoro-1,2-dichloroethane, 1,1-dichloroethane, trichloroethane, tetrachloroethane, 1-fluoro-1,2,2-trichloroethane, 1-bromoethane or 1,1,2-trifluoro-2-chloroethane, or to pass inert gases such as nitrogen, argon, carbon dioxide or air in during the reaction.

The reaction temperature is not critical but the upper limit is determined by the sensitivity of the particular enzyme to temperature. The preferred temperature range is between –30° C. and 60° C., particularly preferably between –10° C. and 10° C.

In a second step, at least bifunctional amines or mixtures of at least bifunctional amines are added. The time between step 1 and 2 is preferably not more than 1 s to 10 min, particularly preferably 30 s to 5 min.

The added at least bifunctional amines react with as yet unreacted functional groups of the monomers to give crosslinking and/or chain extension. The at least bifunctional amines used are primary or secondary amines such as amines of alkanes, alkenes, alkynes, cycloalkanes, cycloalkenes, arenes, alkylarenes, arylalkanes, diaryl ethers, diaryl thioethers, diarylamines, dialkylamines or piperazine dialkanes, it being possible for the aromatic or nonaromatic cyclic groups in these amines in turn to be substituted by one to four $C_1$–$C_4$-alkyl, $C_1$–$C_4$-haloalkyl and/or halogen radicals. Preferred radicals are the amine monomers known from polyurethane and polyamide chemistry.

Particular preference is given to
bis-3-aminopropyl-1,4-piperazine,
bis-3-aminopropyl ether,
bis-2-aminoethyl ether,
N-phenylethylenediamine,
N,N'-diethylethylenediamine,
N,N'-diethylpropylenediamine,
N,N'-diethylbutylenediamine,
N,N'-diethylhexylenediamine,
isophoronediamine,
1,2-diaminocyclohexane (cis and trans),
1,2-diamino-1,2-diphenylethane (cis and trans),
1,8-diaminonaphthalene,
aliphatic amines of the formula II

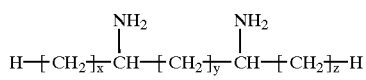

II with
x=0–10
y=0–10
z=0–10
and $0 \leq x+y+z \leq 10$,
such as 1,2-diaminobutane,
1,n-diaminoalkanes, by which are meant linear $C_2$–$C_{12}$-diaminoalkanes with terminal amino functionalities (n=2 to 12; ≡x=0 and z=0 and y=0 to 10), such as
1,2-diaminoethane,
1,3-diaminopropane,
1,4-diaminobutane,
1,5-diaminopentane,
1,6-diaminohexane,
1,7-diaminoheptane,
1,8-diaminooctane,
1,9-diaminononane,
1,10-diaminodecane,
1,11-diaminoundecane or
1,12-diaminododecane,
and in each case the N-monoalkylated or N-monoarylated 1,n-diaminoalkanes (n=2 to 12), and the N-alkylated and N'-arylated, N,N'-dialkylated or N,N'-diarylated 1,n-diaminoalkanes (n=2 to 12).

The choice of the at least bifunctional monomers and of the at least bifunctional amines has a negligible effect on the yield of enzyme-containing polymers. It is therefore possible to use any suitable at least bifunctional monomers and any suitable at least bifunctional amines, and any suitable combinations.

Particularly good polymer and catalyst properties, such as increased useful life and increased conversions, are obtained when, as is evident in Example 2, the at least bifunctional monomer in the first step and at least bifunctional amine in the second step are preferably used in the following combinations:
p-phenylene diisocyanate with 1,n-diaminoalkane,
4-methyl-m-phenylene diisocyanate with 1,n-diaminoalkane,
4,4'-methylenebisphenyl diisocyanate(MDI) with 1,n-diaminoalkane,
p-phenylene diisocyanate with N-phenylethylenediamine,
p-phenylene diisocyanate with 1,6-diaminohexane,
4-methyl-m-phenylene diisocyanate with N,N'-diethylethylenediamine or
4-methyl-m-phenylene diisocyanate with 1,4-diaminobutane.

The enzyme-containing polymers are isolated from the reaction solution by conventional methods for separating solids from fluid systems, e.g. by filtering off and drying the resulting enzyme-containing polymer. When using solvents which lead to tacky polymers, methyl t-butyl ether (MTBE) is preferably added before the filtration, in order to obtain free-flowing products. Without addition of physical blowing agents at the start of the reaction, the enzyme-containing polymers result as amorphous solids. To adapt the solid to particular embodiments of reactors, the amorphous solid can undergo subsequent processing, for example grinding and compressing.

The enzyme-containing polymers according to the invention are used as catalyst in chemical reactions. Chemical reactions mean according to the invention reactions which the enzymes are able to catalyze in the nonimmobilized, free state in solution. The following reactions may be mentioned as examples:

Acylation or enantioselective acylation of alcohols, acylation or enantioselective acylation of amines and amino esters, hydrolysis or enantioselective hydrolysis of esters, acylation or enantioselective acylation of cyanohydrins, hydrolysis or enantioselective hydrolysis of cyanohydrin esters, rendering meso diols asymmetric, rendering meso diesters asymmetric by hydrolysis, epoxidation, oxidation, aldol reactions, amide hydrolyses, cleavage and breakdown of proteins, transesterifications or hydrolysis of epoxides.

A preferred use of enzyme-containing polymer according to the invention, e.g. lipase-containing polymer, is for catalyzing the acylation or enantioselective acylation of alcohols. It is particularly preferred to use in this reaction a polymer which contains lipase from *Burkholderia plantarii* and has been obtained by using the abovementioned preferred combination of at least bifunctional monomers and at least bifunctional amines.

The process for the enzyme-catalyzed conversion of substrates comprises reacting the substrates in the presence of the enzyme-containing polymer. Other reagents are preferably added, depending on what is required by the type of reaction. Thus, for example, an acylation (such as Example 2) requires addition of an acylating agent, whereas, for example, hydrolysis (as Example 4) does not need other reagents to be added. A substrate means according to the invention a chemical compound which can be converted, i.e. chemically altered, by the nonimmobilized free enzymes in solution. In the case of enantioselective transformations, mixtures of stereoisomers, of which only one stereoisomer is converted, are likewise substrates. Examples which may be mentioned are alcohols, amines, amino esters, amides, esters, thioesters, thiols, cyanohydrins, cyanohydrin esters, meso diols, alkenes, proteins, epoxides and halohydrins. The process is preferably carried out in solution, with or without solvent in the case of liquid substrates. Solvents which can be used are liquid solvents such as water or organic solvents, as well as aqueous/organic two-phase mixtures. Organic solvents preferably used are dioxane, THF, diethyl ether, methyl t-butyl ether (MTBE), toluene or heptane. The aqueous/organic two-phase mixture preferably employed is a water/MTBE mixture in any suitable ratio. When the process is carried out in solution, the substrate concentration is not critical, but is preferably between 0.5% by weight and 50% by weight, based on the solution, particularly preferably 20 to 30% by weight. The temperature for carrying out the process is likewise not critical, but an upper limit is set by the stability of the enzyme in the polymer to temperature. The process is preferably carried out at 0° C. to 60° C., particularly preferably 15° C. to 40° C.

The process can be carried out continuously or batchwise. For carrying out the process continuously, a liquid mobile phase is passed, for example, in a manner known per se through a bed of enzyme-containing polymer in a reactor. The mobile phase can be either a solution of substrate (and reagents) or the liquid substrates (and reagents) without solvent. The flow rate is not critical and depends on technical aspects of the process, such as the height, diameter and particle size of the bed and on the design of the reactor. The particle size of the enzyme-containing polymer is likewise not critical in relation to the enzyme activity. Reactors used for the continuous process are preferably the reactors conventional for continuous processes with heterogeneous catalysis (fluid/solid reactions) (J. Hagen, Chemische Reaktionstechnik, VCH, Weinheim 1992, pp. 165–169). Examples which may be mentioned are fluidized bed reactors and fixed bed reactors, such as tubular reactor, column reactor, full space reactor, quench tube reactor, tube bundle reactor and flat bed contact reactor.

When the process is carried out batchwise, the enzyme-containing polymers are suspended in a manner known per se in a solution of substrate (and reagents) or in liquid substrates (and reagents) in a reactor, with or without solvent, and the suspension is mixed. The reactors preferably used for the batchwise process are the reactors conventional for batchwise processes with heterogeneous catalysis (fluid/solid reactions), with shaking, mixing or stirring device. Examples which may be mentioned are stirred vessels and designs generated therefrom, and reaction vessels with a shaking device.

After the reaction is complete (thermodynamic equilibrium reached), the enzyme-containing polymer is isolated, preferably by decantation or filtration and washing with a solvent, and used in further reactions.

In a preferred embodiment of the process, substrates which contain functional groups which can be acylated, e.g. hydroxyl, amino or mercapto groups, such as alcohols, amines or thiols, are acylated with acylating agents in the presence of the enzyme-containing polymer as catalyst.

A particularly preferred process is one for the acylation or enantioselective acylation of alcohols with acylating agents in the presence of a polymer as catalyst, which contains according to the invention a lipase from *Burkholderia plantarii* (see Example 2).

There is virtually no restriction in relation to the alcohols. Thus, it is possible to use monohydric and polyhydric alcohols such as
1-phenylethanol,
2-chloro-1-phenylethanol,
2-chloro-1-(m-chlorophenyl)-ethanol,
3-pentyn-2-ol,
1-butyn-3-ol,
2-hydroxy-4-phenylbutyric esters,
a-methyl-1,3-benzodioxole-5-ethanol,
1-(1,3-benzodioxol-4-yl)-2-propanol,
trans-2-methoxycyclohexanol or
2-methoxy-2-phenylethanol.

Acylating agents mean according to the invention organic compounds which are able to act in the presence of acylating enzymes, such as the lipase from *Burkholderia plantarii,* as acyl donor in solution. Examples which may be mentioned are:

Aliphatic, araliphatic or aromatic carboxylic acids which are optionally substituted by halogen such as Cl, Br, I, F (acylation), such as
$C_1$–$C_6$-alkanecarboxylic acids, e.g. formic acid, acetic acid, propionic acid, butyric acid or
such as araliphatic or aromatic carboxylic acids, e.g. benzoic acid, 3-phenylpropionic acid or
the corresponding carboxylic esters (transesterification) such as 3-phenylpropionic esters or alkyl acetates such as ethyl acetate.

Preferred carboxylic esters as acylating agents are vinyl esters of the formula III

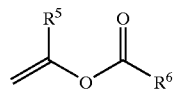

in which
$R^5$ is hydrogen or a $C_1$–$C_4$-alkyl, preferably methyl, group and
$R^6$ is hydrogen, $C_1$–$C_{18}$-alkyl which is optionally substituted by halogen, phenyl or ($C_1$–$C_3$-)alkoxy-($C_1$–$C_4$)-alkyl, such as vinyl formate, vinyl acetate, vinyl propionate or vinyl butyrate.

Further acylating agents are aliphatic, cycloaliphatic, araliphatic or aromatic carboxylic anhydrides and mixed carboxylic anhydrides (acylation), such as acetic anhydride, succinic anhydride (SA), butyric anhydride, 2-ethylhexanoic anhydride or methylsuccinic anhydride.

The process is preferably carried out either in solution or else, in the case of liquid substrates, without solvent. The solvents preferably used for this process are organic solvents. Organic solvents preferably used are ethers, aromatic or aliphatic hydrocarbons, such as dioxane, THF, diethyl ether, methyl t-butyl ether (MTBE), toluene or heptane. When the process is carried out in solution, the substrate concentration is not critical but is preferably between 0.5% by weight and 50% by weight, based on the solution, particularly preferably 20 to 30% by weight. On use of succinic anhydride (SA) or other anhydrides of low solubility as acylating agents it is possible and particularly advantageous to admix propylene carbonate to dissolve the SA. This is particularly important in a continuous process.

The process can, as mentioned above, be carried out continuously or batchwise. In the latter particularly preferred embodiment of the process, in the batchwise case (see Example 2.a) an alcohol and an acylating agent are, as mentioned above, introduced into an aprotic solvent or used without solvent, and a polymer according to the invention, which contains a lipase from *Burkholderia plantarii,* is added. The suspension is mixed during the reaction. The amount of added catalyst is not critical, and the amount of an aliquot, corresponding to free lipase, of the polymer is, in a typical embodiment, preferably about 0.01 to 5% by weight of the alcohol employed as substrate. The reaction time depends on the setting up of the thermodynamic equilibrium and is not critical. The reaction time is generally from 6 h to 24 h. After the reaction is complete, the enzyme-containing polymer is isolated, preferably by decantation or filtration and washing with an aprotic solvent, and used in further reactions. The continuous process is carried out as described above. One example thereof is described in Example 2.b.

The process for the enantioselective enzyme-catalyzed transformation of substrates with the polymers according to the invention can be used to remove stereoisomers and specifically to remove enantiomers from the mixture of stereoisomers in the substrate. The process for the enantioselective acylation of alcohols is preferably used for separating racemic alcohols. The enantioselective substrate specificity of the immobilized lipase means that only one enantiomer of the racemic alcohol is acylated, and the other enantiomer remains behind. The resulting products can easily be separated by chemical, physical and mechanical separation methods in a manner known per se. Examples which may be mentioned are crystallization, precipitation, extraction in two-phase solvent systems and thermal separation processes such as distillation.

The lipase-containing polymers can also catalyze the hydrolysis of esters by adding water and using a preferably two-phase system, e.g. water/MTBE.

The enzyme-containing polymers according to the invention are valuable catalysts for conversions and enantioselective conversions. Compared with the free enzymes, they are distinguished by a long useful life and easy isolation from the reaction mixtures after the reaction is complete. Compared with the prior art, the enzyme-containing polymers according to the invention have the following advantages:

- The polymers can be loaded with a very much greater density of active enzyme species. While the conversion and the useful life remain the same, this achieves higher space-time yields (STY) in enzyme-catalyzed reactions.
- The preparation of the enzyme-containing polymers from organic solution is simpler and thus more economical through the possibility of using monomers from polyurethane chemistry. It is possible to dispense with the preparation of amphiphilic prepolymers.
- The enzyme-containing polymers can be prepared both as foam and as amorphous solid, so that they allow the polymer properties and thus the enzyme activities to be optimized flexibly.
- The enzyme-containing polymers according to the invention have a longer useful life than in the prior art.

The following Examples illustrate the invention:

EXAMPLE 1

Preparation of Enzyme-containing Polymers with Lipase (*Burkholderia plantarii*) as Example a) Immobilization of the lipase by polymerization into a polyurethane made from ethylenediamine and MDI (4,4'-methylenediphenyl diisocyanate) (Table 1, 1A)

500 mg of lipase (*Burkholderia plantarii*) were suspended in 100 ml of toluene, and 40 mmol of MDI were added. After stirring at 0° C. for 1 minute, 40 mmol of ethylenediamine were added. The mixture was stirred at RT for 15 min. Addition of 200 ml of MTBE was followed by filtration with suction, and the solid was dried. Yield: 10.5 g of pale yellow solid.

b) to x) In analogy to this method, the following enzyme-containing polymers were prepared in the stated yields using the diamines (1 to 6) indicated in the rows and the bifunctional monomers (A to D) indicated in the columns. All the enzyme-containing polymers were obtained as pale yellow solids.

TABLE 1

| | | Yield of enzyme-containing polymer | | | |
|---|---|---|---|---|---|
| | | A<br>4,4'-Methylenediphenyl diisocyanate | B<br>p-Phenylene diisocyanate | C<br>4-Methyl-m-phenylene diisocyanate | D<br>p-Phenylene diisothiocyanate |
| 1 | 1,2-Diaminoethane | a)<br>10.5 g | b)<br>8.0 g | c)<br>8.5 g | d)<br>8.9 g |
| 2 | 1,2-Diaminobutane | e)<br>12.5 g | f)<br>9.2 g | g)<br>10.2 g | h)<br>10.0 g |
| 3 | N,N'-Diethylethylenediamine | i)<br>14.3 g | j)<br>10.1 g | k)<br>11.4 g | l)<br>11.2 g |
| 4 | N-Phenylethylenediamine | m)<br>15.0 g | n)<br>11.1 g | o)<br>15.3 g | p)<br>12.3 g |
| 5 | 1,4-Diaminobutane | q)<br>11.9 g | r)<br>9.9 g | s)<br>10.4 g | t)<br>10.9 g |
| 6 | 1,4-Diaminohexane | u)<br>14.0 g | v)<br>10.1 g | w)<br>10.6 g | x)<br>11.2 g |

EXAMPLE 2

Enantioselective Acylation of Racemic 1-phenylethanol as Substrate with Vinyl Propionate as Acylating Agent in the Presence of the Lipase-containing Polymers Prepared in Example 1, and Determination of the Useful Life

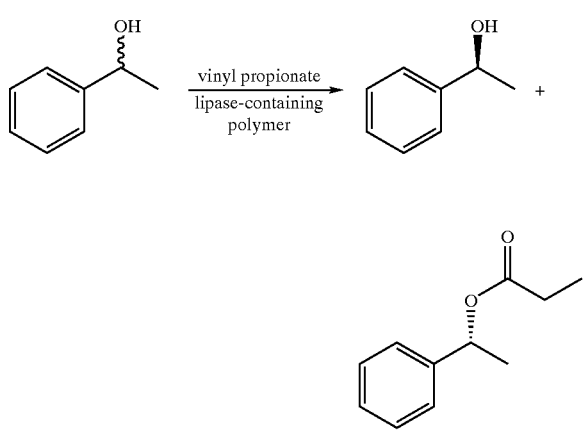

Example 2.a

Batchwise Process

Firstly a stock solution was prepared from 500 g (4.1 mol) of 1-phenylethanol and 246 g (2.46 mol) of vinyl propionate in 2 l of MTBE. 5 ml of this solution were added in each case to an aliquot, corresponding to 10 mg of free lipase, of the lipase-containing polymer. After shaking at RT for 12 h, the lipase-containing polymer was filtered off, and the conversion the enantioselectivity of the acylated antipode were determined by GC and have been listed in Table 2. The filter residues were washed with MTBE and employed again in order to determine the useful life. The experiment was repeated up to 10 times. The lipase-containing polymers used were those prepared in Example 1. For comparison, the analogous experiment with free lipase was carried out.

TABLE 2.1

Conversion (C in [%]) and enantioselectivity (ee in [%]) of the acylated antipode on enantioselective acylation of racemic 1-phenylethanol in the presence of free lipase in a batchwise process. The process was repeated up to 10 times using the lipase isolated from the preceding experiment.

Free lipase

| Run | C | ee |
|---|---|---|
| 1 | 51.6 | 99 |
| 2 | 44.8 | 99 |
| 3 | 42.4 | 99 |
| 4 | 38.4 | 99 |
| 5 | 23.7 | 99 |
| 10 | 11.3 | 99 |

TABLE 2.2

Conversion (C in [%]) and enantioselectivity (ee in [%]) of the acylated antipode on enantioselective acylation of racemic 1-phenylethanol in the presence of the particular lipase-containing polymer in a batchwise process. The process was repeated up to 10 times using the polymers isolated from the preceding experiment.

| Run | c | ee | Run | C | ee | Run | c | ee | Run | C | ee |
|---|---|---|---|---|---|---|---|---|---|---|---|
| a) A1 | | | b) B1 | | | c) C1 | | | d) D1 | | |
| 1 | 44.1 | 99 | 1 | 49.6 | 99 | 1 | 49.3 | 99 | 1 | 42.1 | 99 |
| 2 | 37.8 | 99 | 2 | 50.1 | 99 | 2 | 46.8 | 99 | 2 | 47.0 | 99 |
| 3 | 34.6 | 99 | 3 | 49.5 | 99 | 3 | 41.5 | 99 | 3 | 30.5 | 99 |
| 4 | — | — | 4 | 48.9 | 99 | 4 | — | — | 4 | — | — |
| 5 | — | — | 5 | 43.3 | 99 | 5 | — | — | 5 | — | — |
| 10 | — | — | 10 | — | — | 10 | — | — | 10 | — | — |
| e) A2 | | | f) B2 | | | g) C2 | | | h) D2 | | |
| 1 | 37.7 | 99 | 1 | 49.3 | 99 | 1 | 44.4 | 99 | 1 | 52.0 | 98 |
| 2 | 32.5 | 99 | 2 | 51.5 | 98 | 2 | 49.8 | 99 | 2 | 51.2 | 98 |
| 3 | — | — | 3 | 51.1 | 98 | 3 | 45.9 | 99 | 3 | 43.3 | 99 |
| 4 | — | — | 4 | 45.6 | 99 | 4 | 50.3 | 99 | 4 | 42.1 | 99 |
| 5 | — | — | 5 | 45.9 | 99 | 5 | 48.3 | 99 | 5 | — | — |
| 10 | — | — | 10 | 41.4 | 99 | 10 | 45.6 | 99 | 10 | — | — |
| i) A3 | | | j) B3 | | | k) C3 | | | l) D3 | | |
| 1 | 43.5 | 99 | 1 | 48.2 | 99 | 1 | 47.5 | 99 | 1 | 53.6 | 97 |
| 2 | 44.5 | 99 | 2 | 40.0 | 99 | 2 | 48.8 | 99 | 2 | 49.0 | 99 |
| 3 | — | — | 3 | 51.0 | 98 | 3 | 46.6 | 99 | 3 | 36.4 | 99 |
| 4 | — | — | 4 | 44.3 | 99 | 4 | 47.6 | 99 | 4 | — | — |
| 5 | — | — | 5 | — | — | 5 | 49.4 | 99 | 5 | — | — |
| 10 | — | — | 10 | — | — | 10 | 48.4 | 99 | 10 | — | — |
| m) A4 | | | n) B4 | | | o) C4 | | | p) D4 | | |
| 1 | 50.1 | 99 | 1 | 50.4 | 99 | 1 | 48.9 | 99 | 1 | 49.1 | 99 |
| 2 | 19.5 | 98 | 2 | 47.7 | 99 | 2 | 47.7 | 99 | 2 | 51.6 | 98 |
| 3 | — | — | 3 | 47.3 | 99 | 3 | — | — | 3 | 33.4 | 99 |
| 4 | — | — | 4 | 46.1 | 99 | 4 | — | — | 4 | — | — |
| 5 | — | — | 5 | 49.1 | 99 | 5 | — | — | 5 | — | — |
| 10 | — | — | 10 | — | — | 10 | — | — | 10 | — | — |
| q) A5 | | | r) B5 | | | s) C5 | | | t) D5 | | |
| 1 | 43.9 | 99 | 1 | 50.6 | 99 | 1 | 50.4 | 99 | 1 | 46.3 | 99 |
| 2 | 48.7 | 99 | 2 | 51.4 | 99 | 2 | 42.7 | 99 | 2 | 47.3 | 99 |
| 3 | 43.9 | 99 | 3 | 49.5 | 99 | 3 | 43.7 | 99 | 3 | 46.7 | 99 |
| 4 | 45.1 | 99 | 4 | 42.4 | 99 | 4 | 46.4 | 99 | 4 | 44.3 | 99 |

TABLE 2.2-continued

Conversion (C in [%]) and enantioselectivity (ee in [%]) of the acylated antipode on enantioselective acylation of racemic 1-phenylethanol in the presence of the particular lipase-containing polymer in a batchwise process. The process was repeated up to 10 times using the polymers isolated from the preceding experiment.

| Run | c | ee | Run | C | ee | Run | c | ee | Run | C | ee |
|---|---|---|---|---|---|---|---|---|---|---|---|
| 5 | 43.7 | 99 | 5 | — | — | 5 | 51.0 | 98 | 5 | 43.9 | 99 |
| 10 | 41.8 | 99 | 10 | — | — | 10 | 48.9 | 99 | 10 | — | 99 |
| u) A6 | | | v) B6 | | | w) C6 | | | x) D6 | | |
| 1 | 48.5 | 99 | 1 | 46.1 | 99 | 1 | 45.3 | 99 | 1 | 41.8 | 99 |
| 2 | 47.0 | 99 | 2 | 49.3 | 99 | 2 | 37.3 | 99 | 2 | 45.4 | 99 |
| 3 | 36.8 | 99 | 3 | 51.7 | 98 | 3 | 40.3 | 99 | 3 | 42.9 | 99 |
| 4 | — | — | 4 | 50.2 | 99 | 4 | 37.5 | 99 | 4 | 41.5 | 99 |
| 5 | — | — | 5 | 49.6 | 99 | 5 | — | — | 5 | — | — |
| 10 | — | — | 10 | 49.4 | 99 | 10 | — | — | 10 | — | — |

Example 2.b

Continuous Process

A lipase-containing polymer (B6, Example 1.v)) was packed in a chromatography column with a diameter of 1 cm, and a flow set at 30–35 ml/h of the precursor solution was pumped over the immobilizate by a pump. Samples were taken at regular intervals and the conversion and enantioselectivity were determined by GC and have been listed in Table 4. For comparison, a lyophilizate of free lipase was employed.

TABLE 2.3

Conversion (C) and enantioselectivity (ee) in [%], measured at regular intervals during a continuous process for the enantioselective acylation of racemic 1-phenylethanol. The values for the lipase-containing polymer B6 (Example 1.v)) are compared with the values for the free lipase.

| | Time | | | | | | | | | | | |
|---|---|---|---|---|---|---|---|---|---|---|---|---|
| | 10 h | | 20 h | | 50 h | | 100 h | | 150 h | | 200 h | |
| | C | ee | C | ee | C | ee | C | ee | C | ee | C | ee |
| Free lipase | 54.3 | 97 | 46.7 | 99 | 36.2 | 99 | 24.5 | 99 | 12.0 | 99 | 5.6 | 99 |
| Lipase-containing polymer B6 | 51.5 | 98 | 50.2 | 99 | 48.7 | 99 | 49.5 | 99 | 47.9 | 99 | 48.9 | 99 |

EXAMPLE 3

Effect of the Loading Density on the Activity of the Immobilizates

In analogy to Example 1.v), a lipase-containing polymer B6 was prepared using 500 mg (loading 5% by weight), 100 mg (loading 1% by weight) and 50 mg (loading 0.5% by weight) of lipase (*Burkholderia plantarii*).

In analogy to Example 2.1, the activity and useful life of the lipase-containing polymers for the enantioselective acylation of alcohols were determined.

Firstly a stock solution was prepared from 500 g (4.1 mol) of 1-phenylethanol and 246 g (2.46 mol) of vinyl propionate in 2 l of MTBE. 5 ml of this solution were added in each case to an aliquot, corresponding to 10 mg of free lipase, of the lipase-containing polymer (a correspondingly larger amount of polymer for polymers with a smaller loading). After shaking at RT for 12 h, the lipase-containing polymer was filtered off, and the conversion and the enantioselectivity of the acylated antipode were determined by GC and have been listed in Table 5. The filter residues were washed with MTBE and employed again in order to determine the useful life. The experiment was repeated up to 5 times. For comparison, the analogous experiment with free lipase was carried out.

TABLE 3

Conversion (C in [%]) and enantioselectivity (ee in [%]) of the acylated antipode on enantioselective acylation of racemic 1-phenylethanol in the presence of lipase-containing polymer B6 with varying lipase loading (% by weight) in a batchwise process. The process was repeated 5 times using the polymers isolated from the preceding experiment.

| Loading | Free lipase — | | B6/50 mg lip. 0.5 % | | B6/100 mg lip. 1% | | B6/500 mg lip. 5% | |
|---|---|---|---|---|---|---|---|---|
| Run | C | ee | C | ee | C | ee | C | ee |
| 1 | 51.6 | 99 | 45.3 | 99 | 47.8 | 99 | 46.1 | 99 |
| 2 | 44.8 | 99 | 42.3 | 99 | 50.3 | 99 | 49.3 | 99 |
| 3 | 42.4 | 99 | 39.5 | 98 | 52.5 | 97 | 51.7 | 98 |
| 4 | 38.4 | 99 | 40.2 | 99 | 51.3 | 98 | 50.3 | 99 |
| 5 | 23.7 | 99 | 39.5 | 99 | 49.6 | 99 | 48.9 | 99 |

EXAMPLE 4

Hydrolysis of Esters with Lipase-containing Polymer in Two-phase (Organic/Aqueous) Solvent Systems 10 g of 1-phenylethyl propionate were introduced into 100 ml of MTBE/water (1:1, V/V). Then 10.5 g of lipase-containing polymer (A1) as in Example 1a) were added and the conversion was determined after 3 h by GC. After completion of the reaction (3 h) the lipase-containing polymer was isolated from the reaction solution by filtering off with suction and washing with MTBE and was used in a second analogous design of experiment.

For comparison, an analogous series of experiments was carried out with free lipase. For this, 10 g of 1-phenylethyl propionate were introduced into 100 ml of MTBE/water (1:1, V/V). Then 500 mg of free lipase (*Burkholderia plantarii*) were added and the conversion was determined after 3 h by GC. After completion of the reaction (3 h), the lipase was isolated from the reaction solution by filtration with suction and was used in a second analogous design of experiment.

TABLE 4

Conversion (in [%]) in the hydrolysis of 1-phenylethyl propionate in the presence of lipase-containing polymer A1 (Example 1.a)) or of free lipase in a batchwise process. The process was repeated with the isolated polymer and with the isolated free lipase.

| Lipase-containing polymer (A1) | | Free lipase | |
|---|---|---|---|
| Run | Conversion (3h; [%]) | Run | Conversion (3h; [%]) |
| 1 | 10.5 | 1 | 12.4 |
| 2 | 10.0 | 2 | 2.4 |

Comparative Example 1

Preparation of an Enzyme-containing Polymer by Reacting an Aqueous Enzyme Suspension with Polyisocyanate Prepolymers with Lipase (*Burkholderia plantarii*) as Example 17.2 g of B278 prepolymer (BASF AG trademark; prepolymer consisting of MDI-capped PO (polypropylene oxide; 25%) and EO (ethylene oxide; 75%) spacer units (the OH number is about 6500)) were stirred while 1 ml of a 10% solution (% by weight) of lipase (*Burkholderia plantarii*) in water was added. Foam formation started with evolution of gas and was complete after about 30 min. The foam was washed with 100 ml of MTBE and dried.

The resulting product showed no activity in the experiment of Example 2 (enantioselective enzymatic acylation).

We claim:

1. A process for preparing an enzyme-containing polymer, which comprises, in a first step, reacting an enzyme in an organic solvent with an at least bifunctional monomer having the formula $$R^1(X)_s(Y)_t$$

where
- $R^1$ is an alkane, alkene, cycloalkane, cycloalkene, arene, arylalkane, diaryl ether, diaryl thioether or diarylamine group, and wherein if $R^1$ is cyclic it is optionally substituted by from one to four $C_1$–$C_4$-alkyl, $C_1$–$C_4$-haloalkyl and/or halogen radicals,
- s has a value of from 0 to 5,
- t has a value of from 0 to 5, and
- s+t has a value of from 2 to 5, and
- X is isocyanate,
- Y is isothiocyanate, or
- X═Y is —$COR^3$, and
- $R^3$ is a leaving group which can be displaced by the amino, hydroxyl or mercapto functionality of the enzyme, and in a second step, adding an at least bifunctional amine or a mixture of at least bifunctional amines.

2. A process as claimed in claim 1, wherein the bifunctional amine has the formula $$H_2N-(CH_2)_n-NH_2,$$

with n being an integer from 2 to 12, and the bifunctional monomer is selected from the group consisting of p-phenylene diisocyanate, 4-methyl-m-phenylene diisocyanate, and 4,4'-methylenebisphenyl diisocyanate (MDI).

3. A process as claimed in claim 1, wherein the bifunctional monomer is p-phenylene diisocyanate, and the bifunctional amine is selected from the group consisting of N-phenylethylenediamine and 1,6-diaminohexane.

4. A process as claimed in claim 1, wherein the bifunctional monomer is 4-methyl-m-phenylene diisocyanate, and the bifunctional amine is selected from the group consisting of N,N'-diethyl-ethylenediamine and 1,4-diaminobutane.

5. A process as claimed in claim 1, wherein enzymes which have an enzymatic activity in organic solvents are used.

6. A process as claimed in claim 1, wherein the enzyme is selected from the group consisting of lipases, amidases, esterases, haloperoxidases, proteases and hydrolases.

7. A process as claimed in claim 1, wherein the time between the first and second steps is not more than 1 second to 10 min.

8. A process as claimed in claim 1, wherein, before the reaction, a physical blowing agent is mixed with the reaction solution.

9. An enzyme-containing polymer obtainable by a process as claimed in claim 1.

10. A process for the enzyme-catalyzed transformation or enantioselective transformation of substrates, which comprises reacting the substrates in the presence of the enzyme-containing polymer as claimed in claim 9.

11. A process as claimed in claim 10, wherein alcohols are used as substrates and are acylated or enantioselectively acylated.

12. A process as claimed in claim 10, wherein mixtures of stereoisomers or racemates of alcohols are used as substrates and are enantioselectively acylated, and the mixtures are then fractionated.

13. A process for catalyzing a chemical reaction wherein an enzyme-containing polymer as claimed in claim 9 is used as catalyst.

14. A process as claimed in claim 13, wherein the enzyme-containing polymer is used as catalyst for the acylation or enantioselective acylation of alcohols.

* * * * *